United States Patent [19]

Sela

[11] Patent Number: 4,980,161
[45] Date of Patent: Dec. 25, 1990

[54] METHOD OF TREATING VIRAL INFECTION IN PLANTS

[76] Inventor: Ilan Sela, Moskovitz 20, Rehovot, Israel

[21] Appl. No.: 645,378

[22] Filed: Aug. 29, 1984

Related U.S. Application Data

[63] Continuation of Ser. No. 352,407, Feb. 25, 1982, abandoned.

[51] Int. Cl.$^5$ .................... A61K 37/66; A01H 1/00; A01N 43/02
[52] U.S. Cl. .................. 424/85.4; 424/85.6; 424/85.7; 435/811; 47/58; 71/79
[58] Field of Search ............. 435/238, 240, 267, 811, 435/68, 946; 424/85, 85.4, 85.6, 85.7; 47/58; 71/79

[56] References Cited

PUBLICATIONS

Stewart II, W., 1979, pp. 50, 63-64, In: Inferferons and their Actions, CRC Press Inc., Cleveland, Ohio.
Stewart II, W., 1981, pp. 134-145, In: The Interferon System, 2nd Edition, Springer-Verlap: New York, N.Y.
Mozes et al., 1978, J. Am. Virol., 38:241-249.
Misawa et al., 1974, pp. 405-427, In: Tissue Culture and Plant Science, Street, H., ed., Academic Press: New York.
Goeddel et al., 1980, Nature, 287:411-416.
Vincente et al., "Human Interferon Protects Plants Against Several Viruses", Sixth International Congress of Virology, Sendai, Japan, Sep. 1-7, 1984, pp. 35-36.
Ogarkov et al., "Suppression of Reproduction of Potatoe Viruses Under the Effect of Human Interferon", Reports of USSR Academy of Sciences, vol. 276, No. 3, 1984.
Orchansky, et al., Human Interferons Protect Plants from Virus Infection, Proc. Nat'l Acad. Sci., U.S.A., vol. 79, pp. 2278-2280.
Carter et al., Journal of Biological Response Modifiers, 1985, 4:447-459.

*Primary Examiner*—Charles F. Warren
*Assistant Examiner*—David T. Fox
*Attorney, Agent, or Firm*—George M. Gould; William H. Epstein; John J. Schlager

[57] ABSTRACT

There is disclosed a method of treating or preventing viral infections in plants wherein an animal interferon is applied to the plants.

5 Claims, 3 Drawing Sheets

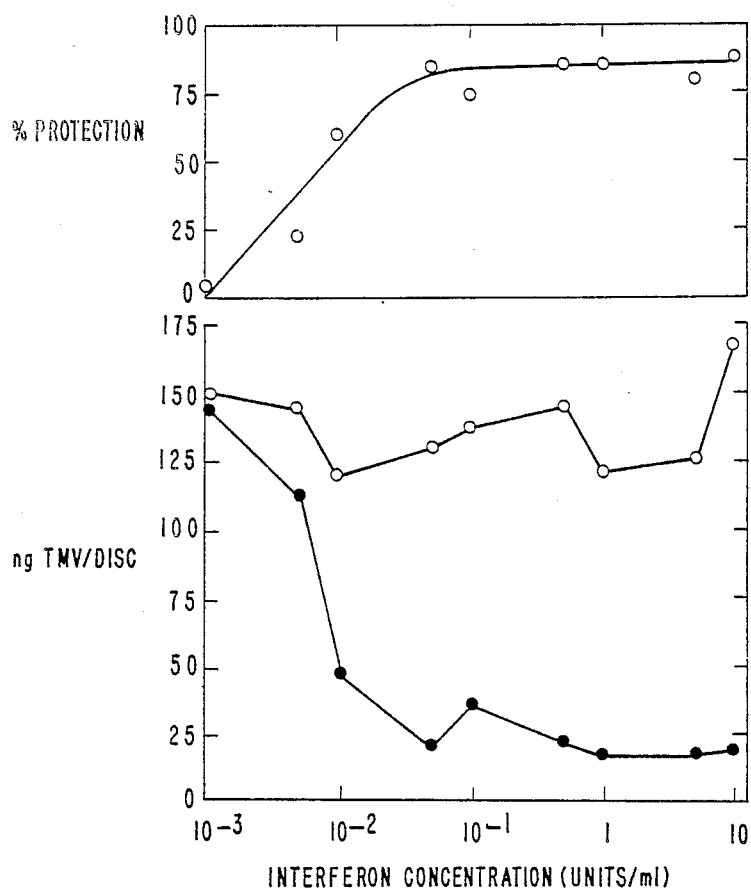
F I G. 1

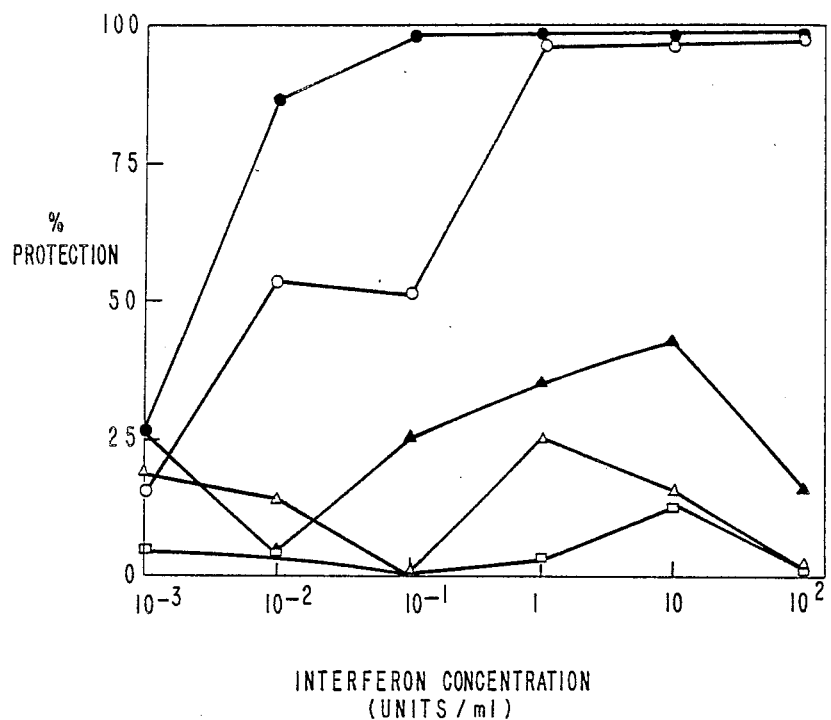
F I G. 3

METHOD OF TREATING VIRAL INFECTION IN PLANTS

The present application is a continuation of application Ser. No. 352,407 filed Feb. 25, 1982, now abandoned.

BACKGROUND OF THE INVENTION

This invention relates to the treatment and prevention of viral infections in plants. More particularly, it relates to the use of animal interferons as agents for the treatment of viral infections in plants.

Viral infections in plants represent a severe problem in agriculture. Citrus crops, tobacco and potatoes are examples of important crops which can be severely damaged by viral infections. Not only can plants be infected in the field, but also viral infection can be passed on from one generation to the next as plants are propagated. The problem of viral infection in potatoes is so pervasive that great effort and sums of money must continually be expended to raise virus-free "germ stock". This germ stock must be grown in a geographical area which is known to be relatively free of vectors (e.g., insects) which transmit potato viruses. Moreover, the germ stock must be grown under scrupulously controlled conditions to assure that it is not exposed to infection. Even when these precautions have been taken, however, there is no certainty that the germ stock will be totally virus free. Once the virus-free germ stock is exported and used as seed in an area where viral transmission is prevalent, the resulting potato crop cannot thereafter be used to seed the next season's crop because of the likelihood of infection in the field. Rather, the farmer must purchase new virus-free stock to seed his crop each year.

An effective means of treating viral infections in plants and/or an efficient means of producing virus-free germ stock would be of considerable value in agriculture.

It is known that the cells of plants respond to viral infection by producing a substance (believed to be proteinaceous) which confers a degree of immunity to viral infection upon surrounding uninfected cells (Sela, *Biochemical Sciences*, Feburary 1981, pp. 31–33). This substance has been given the name "antiviral factor" or "AVF". However, AVF has not been purified to homogeneity, nor has its chemical structure been elucidated.

BRIEF DESCRIPTION OF THE DRAWINGS

FIG. 1 is a graph depicting the effect of homogeneous human leukocyte interferon (species $\gamma_3$) on tobacco mosaic virus in tobacco leaves. The content of tobacco mosaic virus in interferon-treated discs ( ) and in buffer-treated control discs (o) of tobacco leaf is plotted in the lower graph. The percentage of protection against tobacco mosaic virus conferred by treatment with the interferon is plotted in the upper graph.

FIG. 3 is a graph depicting the effect of human fibroblast interferon on tobacco mosaic virus multiplication in tobacco leaves. The various lines on the graph show the results using interferon which has been pretreated with glycosidases bound to sepharose beads for 3 hours (o) and 24 hours ( ); fibroblast interferon which has been pretreated with sepharose beads having no glycosidase bound thereto for 3 hours (Δ) and 24 hours ( ); and untreated fibroblast interferon (□).

DESCRIPTION OF THE INVENTION

Figure 2:
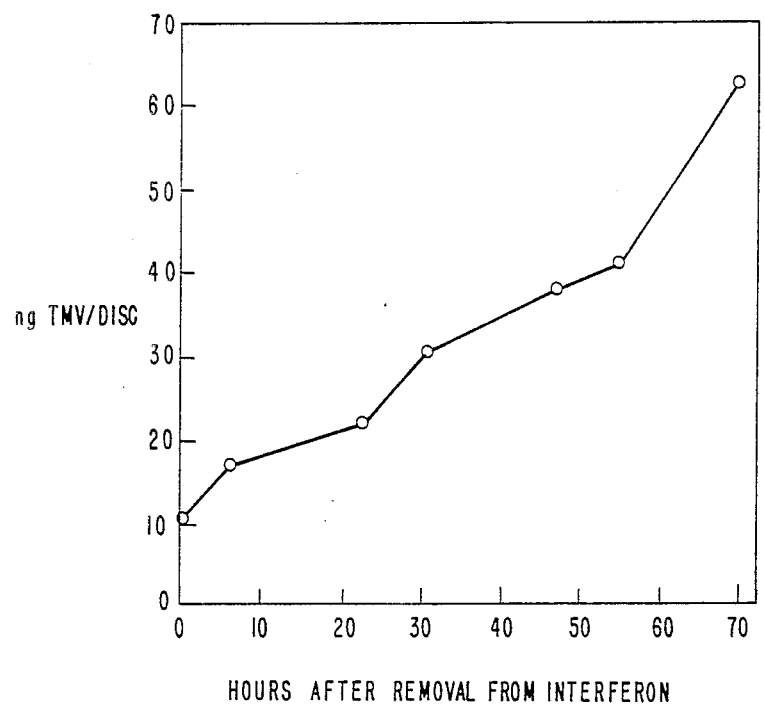
FIG. 2 is a graph plotting infectivity of tobacco mosaic virus in tobacco leaf discs as a function of time after removal of the discs from an interferon solution.

The present invention is based on the discovery that the treatment of virus-infected plants with animal interferons inhibits the spread of viral infection. Accordingly, there is provided a method of treating a viral infection in a plant which involves administering an animal interferon to the infected plant.

The above-mentioned discovery can also be employed in a prophylactic manner; that is, viral infection of a plant can be prevented by treating the plant with an animal interferon prior to the plant being exposed to the virus.

There is also provided, in accordance with the teachings of this invention, a means of producing virus-free germ stock wherein cells taken from a mature plant are propagated in a cell culture medium containing an animal interferon. The newly propagated cells thus produced are virus free, even if the parent cells were virus infected. The newly propagated virus-free cells are then removed from the culture containing the original cells and are separately propagated to produce virus-free plants. These plants can then be used as virus-free germ stock.

The existence of animal interferons has been known for some time (see, e.g., U.S. Pat. No. 3,699,222). Interferons are proteins which are produced by animal cells in response to infection by an inducing agent such as a virus and which inhibit the proliferation of virus in uninfected cells. The production of interferons has been observed in numerous species; for example, in chickens, pigs, mice, monkeys and humans. The antiviral activity of interferons has been noted to be relatively species specific; that is, interferon produced by cells of one species is usually not very effective in protecting cells of a different species against viral infection. In view of its species specificity among animal species, it was quite surprising that animal interferons were effective in inhibiting virus multiplication in plants.

Human interferons have been classified into the three classes of leukocyte, fibroblast and immune interferons. Recently, interferon produced by human leukocytes has been purified to homogeneity (Rubinstein et al., *Proc. Natl. Acad. Sci. U.S.A.*, 76, 1976) and a number of distinct human leukocyte interferon species have been identified (Rubinstein et al., *Arch. of Biochem. & Biophys.*, 210, No. 1, August, pp. 307–318, 1981). Similarly, interferon produced by human fibroblasts has been purified to homogeneity (Friesen et al., *Arch. of Biochem. & Biophys.*, 206, No. 2, February, pp. 432–450, 1981).

Using techniques of genetic recombination, it is now possible to insert exogenous genetic information coding for the amino acid sequence of an interferon molecule into a host microorganism, under the control of a promoter-operator gene sequence, so that the microorganism will express the interferon molecule. Human leukocyte interferons and human fibroblast interferon have been produced in this manner. It is also possible, using techniques of genetic recombination, to produce hybrid interferon molecules which comprise segments of one species of interferon molecule in sequence with segments of one or more different species of interferon molecule(s). As used herein, the term "interferon" or "animal interferon" includes all substances having the molecular structure of interferon, regardless of their method of production (i.e., whether produced by their natural cells of origin or by recombinant DNA techniques or any other techniques). Moreover, these terms include hybrid interferons and biologically active fragments of interferons, even though these may not be produced naturally by animal cells.

As previously indicated, there is provided herein a method for the treatment or prevention of virus infection in plants which comprises applying an animal interferon to the plant. The interferon can be applied in any form in which it is known to be stable. Typically, an aqueous buffered solution (0.01M Na-phosphate, pH 7.6) was employed. The effective concentration of interferon employed may vary somewhat depending on the particular plant being treated, the type of virus and the species of interferon employed. It is well within the skill of the average worker in the art to determine an appropriate concentration without undue experimentation.

It has been found that human leukocyte interferon (species $\gamma_3$) reduced the infectivity of tobacco mosaic virus by 50% when applied to the leaves of tobacco (*Nicotinia tobacum*, L.) at concentrations of from $10^{-1}$ to $10^{-3}$ Units/ml. This indicates a tenfold to ten-thousandfold greater sensitivity of the plant tissue than the reference animal cells. While there is no strict upper limit on the concentration of interferon which can be employed, no particular advantage is seen in using a concentration of greater than about $10^4$ Units/ml. The interferon can be applied to the plant in any convenient manner, for example by spraying or wiping the leaves of the plant with a composition containing the interferon.

It is known that naturally produced human fibroblast interferon, i.e. interferon produced by induced human fibroblast cells, is normally glycosylated. I have found that human fibroblast interferon has a considerably greater antiviral effect in plants when it is deglycosylated. Thus it is preferred to treat human fibroblast interferon with a deglycosylating agent, such as a glycosidase enzyme, prior to employing it as a plant antiviral agent. Since interferon produced by genetically modified bacteria generally is not glycosylated, such treatment is not necessary when employing a human fibroblast interferon so produced.

Because of their ability to inhibit virus multiplication in plants, animal interferons can be employed to grow virus-free germ stock from culture medium. It is known that individual cells can be taken from a mature plant, be placed in a culture medium and grown under appropriate conditions to produce a mature, differentiated plant. Those skilled in the art are familiar with the growth media which can be employed for this purpose.

By adding animal interferon to the growth medium, the newly propagated cells will be virus free, even if the original cells were virus infected. The newly propagated virus-free cells can be separated from the parent cells and placed in a fresh culture medium where they will grow to produce a virus-free plant. The virus-free plant can then be propagated in soil to produce virus-free germ stock. This method is particularly well suited to producing virus-free germ stock for use in potato farming. Since the germ stock produced in this manner will be totally virus-free, it may even be possible to employ potatoes from the resulting crop as seed for the following season's crop.

The following examples are presented in order to further exemplify the invention described herein and not to limit it in any way. While the examples herein relate to the treatment of tobacco mosaic virus, the methods of this invention are equally applicable to other viruses which infect plants, such as potato virus Y and tristesa virus in citrus crops.

Preparation of Interferons

The following human interferons were employed in the examples:

Human leukocyte interferon (IFL): Leukocyte interferon was produced by leukocytes isolated from buffy coat fraction of whole blood from normal donors induced by Newcastle disease virus. The interferon was purified by the procedure described in Proc. Natl. Acad. Sci. U.S.A., 76, No. 2, 640–644, February 1979. The material employed was from the pooled $\alpha$, $\beta$ and $\gamma$ peaks (100,000 Units/ml).

Human leukocyte interferon $\gamma_3$ (IFL $\gamma_3$): Leukocyte interferon was produced from leukocytes of patients with chronic myelogeneous leukemia by induction with Newcastle disease virus. The interferon was purified according to the procedure described in *Arch. of Biochem. and Biophys.*, 210, No. 1, August, 307–318, 1981. The $\gamma_3$ fraction ($2\times 10^8$ units/mg protein, m.w. 18,500) was employed.

Recombinant human leukocyte interferon A (IFL-rA): Leukocyte interferon was obtained from bacteria containing recombinant DNA having the full-length gene for leukocyte interferon (species A) as described in Nature, 287, 411–416, 1980 and purified on a monoclonal antibody immunoadsorbent column to $2\times 10^8$ units/mg of protein.

Human leukocyte interferon $d_1$ (IFL-$d_1$): Leukocyte interferon was produced from a continuous human myeloblast cell line induced with Sendai virus and purified by the procedure described in *J. Biol. Chem.*, 1982, in press (a copy of which is attached as Appendix A). The $d_1$ fraction produced in this manner ($3\times 10^8$ units/mg of protein, m.w. 19,500) was employed.

Human fibroblast interferon (IFF): Human fibroblast interferon was prepared and purified by the procedure described in *Proc. Nat'l. Acad. Sci. U.S.A.*, 77, No. 10, 5716–5719, October 1980.

EXAMPLE 1

Glycosidase Treatment of IFF

A mixture of glycosidases from the livers of the gastropod *Turbo cornutus* (Miles), which exhibited 12 different glycosidase activities, was ligated to beads of cyanogen bromide activated Sepharose 4B according to the procedure described in *Ann. Rev. Biochem.*, 40, 259–278, 1971. The various glycosidase activities of the bound enzymes were examined by the release of p-nitrophenol from the respective p-nitrophenol ethers of the various sugars as described in *J. Biochem.*, 62, 700 et seq., 1967. The activities of the various enzymes were preserved upon ligation.

The IFF (in 0.05M phosphate-citrate buffer pH 4.0; 0.34M NaCl) was placed in a rolling bottle and rotated with the glycosidase-bound Sepharose beads, in one instance for three hours and in another instance for 24 hours, at room temperature. As controls, two additional portions of IFF were rotated with glycine-blocked Sepharose beads for three hours and 24 hours, respectively.

EXAMPLE 2

Antiviral Activity of IFL α

Leaves of tobacco "Samsun" were inoculated with tobacco mosaic virus (5 µg/ml of 0.01M sodium phosphate, pH 7.6). Discs 6.5 mm in diameter were punched out of the leaves into a water-containing beaker. The discs were then distributed randomly in Petri dishes, 20 discs per dish. One hour after inoculation, buffered solutions of IFL α at various dilutions were applied to the discs in the Petri dishes. There were employed as controls inoculated discs to which there were applied only a pyridine/formic acid/propanol buffers at the same dilution factors as the interferon. There were also employed as controls discs which were not inoculated with tobacco mosaic virus. The virus was allowed to multiply for 70–80 hours at room temperature, after which the discs were frozen. The frozen discs were homogenized in a Teflon ®-coated, motor-driven tissue grinder in sodium phosphate buffer (pH 7.6, 0.1 ml. per disc).

The degree of multiplication of tobacco mosaic virus was determined in the homogenates by enzyme-linked immunosorbent assay essentially according to the procedure described in *J. Gen. Virol.*, 34, 475–483, 1980 with the following modifications. The gamma-globulin fraction of serum from chicken immunized against tobacco mosaic virus was adsorbed onto the microplates. Tobacco mosaic virus or the disc homogenate was added after which gamma-globulin from rabbit immunized against TMV was applied. Finally anti-rabbit IgG conjugated to alkaline phosphatase was added. A series of tobacco mosaic virus solutions at known concentrations were incorporated into every microtiter plate to serve as an internal calibration p-nitrophenol was then added as substrate and a yellow color developed. Linearity of absorbance (at 405 nm) with tobacco mosaic virus concentrations was obtained along about 2 logs (10 ng-1 µg/ml).

The amount of tobacco mosaic virus infection in the disc homogenates (ng/disc) was plotted against concentration of either interferon, in the case of the treated discs, or pyridine/formic acid/propanol, in the case of the buffer-treated controls. The results are presented in the lower graph in FIG. 1, wherein ( ) represents treated discs and (o) represents the control discs. The degree of protection against TMV infection conferred by IFL α was determined, at each test concentration of interferon or control buffer, according to the following formula:

$$\frac{ngTMV/disc \text{ (buffer control)} - ngTMV/disc \text{ (interferon treated)}}{ngTMV/disc \text{ (buffer control)}} \times 100 = \% \text{ Protection}$$

The degree of protection was plotted against interferon concentration and the results are presented in the upper graph in FIG. 1. It can be seen from FIG. 1 that the interferon treated discs were protected against TMV infection and that the degree of protection increased with increasing concentration of interferon.

EXAMPLE 3

Infectivity Tests of TMV-Inoculated Leaves Protected by IFL α

Homogenates of tobacco leaf discs pretreated with IFL α (750 Units/ml.) were prepared in a manner similar to that described in Example 2 and inoculated onto 12 half-leaves of *Datura stramonium* L. The opposite half of each leaf was inoculated with the corresponding buffer control-pretreated disc. The infectivity of the disc homogenates was indicated by the induction of local necrotic lesions on the leaves. After incubation for 4 days at 24° C., the lesions on each half leaf were counted. The results are presented in the table below. The results indicate that, while the control-treated discs were infectious, only occasional lesions appeared following inoculation with the interferon-treated disc homogenates. The percentage protection against TMV was calculated for each leaf pair by the formula given in Example 2. Average percentage of protection against TMV for all leaves tested was 93%.

| Number of Local Lesions on *D. Stramonium* Half-Leaves Inoculated with Disc Homogenates ||
| --- | --- |
| Buffer treated control | IFL α-treated disc homogenate |
| 28 | 1 |
| 17 | 0 |
| 35 | 2 |
| 24 | 2 |
| 13 | 0 |
| 36 | 3 |
| 12 | 1 |
| 21 | 1 |
| 25 | 0 |
| 37 | 5 |
| 32 | 4 |
| 28 | 2 |

EXAMPLE 4

Duration of Antiviral Activity

Discs which were punched from leaves of tobacco "Samsun" were immersed in IFL-γ₃ (1 Unit/ml.) one hour after being inoculated with TMV. Beginning seven hours after the immersion in interferon, sample discs were periodically removed from the interferon and placed in a buffer solution containing no interferon. After 77 hours all the discs had been removed from the interferon. All the sample discs were then tested for TMV infection by enzyme linked immunosorbent assay as described in Example 2. The degree of TMV infection (ng./disc) was plotted against the length of time after removal from the interferon. Results are presented in the graph in FIG. 2. Control discs which were not immersed in the interferon had a TMV content of 74 ng./disc.

EXAMPLE 5

Antiviral Activity of Human Leukocyte Interferon

Using the procedure described in Example 2, the antiviral effect against TMV was determined for IFL; IFL-d₁; and IFL-rA. The level of TMV infection was determined in a manner similar to that described in Example 2 for each of the leukocyte interferons at various concentrations. The results, which are presented in the table below, demonstrate that all of the leukocyte interferons tested displayed a concentration-dependent protective effect against TMV infection.

| Interferon concentration | ng./TMV per Disc Treated with Interferon | | |
|---|---|---|---|
| (Units/ml.) | Unfractionated | IFL-d$_1$ | IFL-rA |
| 0 | 63 | 63 | 68 |
| 0.001 | 26 | 48 | 50 |
| 0.01 | 17.5 | <8 | 25 |
| 0.1 | 8.8 | <8 | 25 |
| 1.0 | <8 | <8 | <10 |
| 10.0 | <8 | <8 | <10 |
| 100.0 | — | — | <10 |

EXAMPLE 6

Antiviral Activity of IFF

Using a procedure similar to that described in Example 2, the percentage of protection against TMV infection was determined for varying concentrations of untreated IFF; IFF which had been pretreated for 3 hours or 24 hours with glycine-blocked Sepharose beads; and IFF which had been pretreated for 3 hours or 24 hours with Sepharose beads conjugated to glycosidase as described in Example 1. The results are presented in the graph of FIG. 3. In the graph (□) represents untreated IFF: (Δ) and ( ) represent, respectively, IFF which was treated for 3 hours and 24 hours with glycine-blocked Sepharose beads; (o) and ( ) represent, respectively, IFF which was treated for 3 hours and 24 hours with Sepharose beads conjugated to glycosidase. It can be seen from the graph that the IFF which was deglycosylated by treatment with glycosidase-conjugated Sepharose beads for 3 hours or 24 hours exhibited a considerably higher protective activity than untreated IFF or IFF which had been pretreated with glycine-blocked Sepharose beads.

EXAMPLE 7

Infectivity Tests of TMV-Inoculated Leaves Protected by IFF

Using a procedure similar to that of Example 2, leaves of tobacco "Samsun" were inoculated with TMV and discs therefrom were treated with either control buffer or a solution of IFF (750 Units/ml.). After the TMV was allowed to multiply 70–80 hours, disc homogenates were prepared in the same manner as in Example 2. The infectivity of the disc homogenates was determined by applying the control buffer homogenates and interferon-treated homogenates to half leaves of *Datura stramonium* L. in the same manner as in Example 3. After incubation for 4 days at 24° C., the lesions on each half leaf were counted. The results are presented in the table below. The results indicate that the homogenates of the discs treated with IFF were considerably less infectious than the homogenates of the discs treated with the control buffer. The percentage protection against TMV was calculated for each leaf pair by the formula given in Example 2. Average percentage protection against TMV for all leaves tested was 62%.

| Number of Local Lesions on *D. stramonium* Half-Leaves Inoculated with Disc Homogenates | |
|---|---|
| Buffer-treated control | IFF-treated disc homogenate |
| 21 | 7 |
| 32 | 9 |
| 45 | 19 |
| 12 | 2 |
| 18 | 4 |
| 25 | 11 |
| 9 | 3 |
| 14 | 5 |
| 10 | 1 |
| 28 | 14 |
| 24 | 13 |
| 17 | 10 |

I claim:

1. Method of inhibiting a viral infection in a tobacco plant which comprises applying to the plant a virus inhibiting amount of a human interferon.

2. A method according to claim 1 wherein said virus is tobacco mosaic virus.

3. A method according to claim 2 wherein said interferon is selected from the group consisting of human leukocyte interferon, human fibroblast interferon and deglycosylated human fibroblast interferon.

4. A method according to claim 3, wherein said interferon is produced by a microorganism containing an exogenous gene encoding for the production of said interferon.

5. A method according to claim 4, wherein said gene encodes IFL-rA.

* * * * *